United States Patent
Wei et al.

(10) Patent No.: US 6,455,274 B1
(45) Date of Patent: *Sep. 24, 2002

(54) HUMAN DNA LIGASE IV

(75) Inventors: Ying-Fei Wei, Darnestown, MD (US); William A. Haseltine, Washington, DC (US)

(73) Assignee: Human Genome Sciences, Inc., Rockville, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/461,562

(22) Filed: Jun. 5, 1995

Related U.S. Application Data

(63) Continuation-in-part of application No. PCT/US94/12922, filed on Nov. 8, 1994.

(51) Int. Cl.⁷ .................. C12N 15/52; C12N 15/12; C12N 15/62; C12N 15/63
(52) U.S. Cl. .................. 435/69.1; 435/69.7; 435/325; 435/320.1; 536/23.2; 536/23.1; 536/23.4; 536/23.5; 536/24.3; 536/24.31
(58) Field of Search ............. 536/23.2; 435/252.3, 435/183, 69.1, 254.11, 325, 320.1

(56) References Cited

FOREIGN PATENT DOCUMENTS

WO 96/14394 * 5/1996

OTHER PUBLICATIONS

Wei et al. Molecular cloning and expression of human cDNAs encoding a novel DNA ligase IV and DNA ligase III, an enzyme active in DNA repair and recombination. Molecular and Cellular Biology. vol.15, No.6, pp. 3206–3216, Jun. 1995.*

Hillier et al. yg74h09.r1 Homo sapiens cDNA clone 39274, EST–STS Assession No. R54358, May 18, 1995.*
Sambrook et al. In Molecular Cloning: A Laboratory Manual. Cold Spring Harbor Laboratory Press, Cold Spring Harbor. Chapters 9 and 11, 1989.*
Database Embl, Accession No. Z4289, Nov. 6, 1994.
Wei et al., *Molecular and Cellular Biology*, 15(6):3206–3216 (1995).
PCT International Search Report.
Alan E. Tomkinson, et al., Nucleic Acids Research, vol. 21, No. 23, pp. 5425–5430 (1993).
Alan E. Tomkinson, et al., The Journal of Biological Chemistry, The American Society for Biochemistry and Molecular Biology, Inc., vol. 266, No. 32, Issue of Nov. 15, pp. 21728–21735 (1991).
Deborah E. Barnes, et al., Biochemistry, Proc. Natl. Acad. Sci. USA, vol. 87, pp. 6679–6683 (Sep./1990).
Keith W. Caldecott, et al., Molecular and Cellular Biology, American Society for Microbiology, vol. 14, No. 1, p. 68–76 (1994).
Claude Prigent, et al., Molecular and Cellular Biology, American Society for Microbiology, vol. 14, No. 1, pp. 310–317 (1994).
Thomas Lindahl, et al., Annu. Rev. Biochem., Annual Reviews Inc., vol. 61, pp. 251–81 (1992).
Deborah E. Barnes, et al., Cell, Cell Press, vol. 69, pp. 495–503 (1992).

* cited by examiner

*Primary Examiner*—Michael Pak
(74) *Attorney, Agent, or Firm*—Human Genome Sciences, Inc.

(57) ABSTRACT

A human DNA Ligase IV polypeptide and DNA (RNA) encoding such polypeptide and a procedure for producing such polypeptide by recombinant techniques is disclosed. Also disclosed are methods for utilizing such polypeptide via gene therapy for the treatment of disorders associated with a defect in DNA Ligase IV. Antagonists against such polypeptides and their use as a therapeutic to destroy unwanted cells are also disclosed. Diagnostic assays to detect mutant DNA Ligase IV genes are also disclosed.

46 Claims, 15 Drawing Sheets

Figure 1A

```
           -250                 -230                 -210
             .                    .                    .
CCACAGGCGCTGTAGACTGCCGCCGCATTAGAAGCCTGGCCTGGCCTCCTGATGCTGTGCTCTTCATCTAGACCCAA
-+----+----+----+----+----+----+----+----+----+----+----+----+----+----+----+-
GGTGTCGCGACATCTGACGCGGCGTAATCTTCGGACCGGAGGACTACGACACGAGAAGTAGATCTGGGTT

-190                 -170                 -150
             .                    .                    .
GCCCCAGGTCGTGGGACGATTTCTCCCGTTTTTGACTCCCTGGAACTGTATTGCCTGCTTTACCTGCGTA
-+----+----+----+----+----+----+----+----+----+----+----+----+----+----+----+-
CGGGGTCCAGCACCCTGCTAAAGAGGGCAAAAACTGAGGGACCCTTGACATAACGGACGAAATGGACGCAT

-130                 -110                  -90                  -70
             .                    .                    .                    .
CATGTTGATTCTTCTTTCTCATGGCAACCCCGCAGGAAACCATCAAGATCTCATTTACAGCTGGGATTCTCT
-+----+----+----+----+----+----+----+----+----+----+----+----+----+----+----+-
GTACAACTAAGAAGAGTACCGTTGGGGCGTCCTTTGGTAGTTCTAGAGTAAAATGTCGACCCTAAGAGA

-50                  -30                  -10
             .                    .                    .
GGTTCACAGAGGTAACGGAGCTTGCCCGAGGCCAGTTAAACGAGAAGATTCATCACCGCTTTGATGGCTG
-+----+----+----+----+----+----+----+----+----+----+----+----+----+----+----+-
CCAAGTGTCTCCATTGCCTCGAACGGGCTCCGGTCAATTTGCTCTTCTAAGTAGTGGCGAAACTACCGAC
                                                         M   A   A
```

Figure 1B

```
                    30                    50                       70
        .            .          .          .           .            .
CCTCACAAACTTCACAAACTGTTGCATCTCACGTTCCTTTTGCAGATTGTGTTCAACTTTAGAACGAAT
-+----|----+----|----+----|----+----|----+----|----+----|----+----|--
GGAGTGTTTGAAGTGTTTGACAACGTAGAGTGCAAGGAAAACGTCTAAACACAAGTTGAAATCTGCTTA
 S  Q  T  V  A  S  H  V  P  F  A  D  L  C  S  T  L  E  R  I 90                    110                      130
        .            .          .          .           .            .
ACAGAAAAGTAAGGACGTGCAGAAAAAATCAGACACTTCAGGGAATTTTTAGATTCTTGGAGAAAATTT
-+----|----+----|----+----|----+----|----+----|----+----|----+----|--
TGTCTTTTCATTCCTGCACGTCTCTTTTTAGTCTGTGAAGTCCCTTAAAAATCTAAGAACCTCTTTTAAA
 Q  K  S  K  G  R  A  E  K  I  R  H  F  R  E  F  L  D  S  W  R  K  F 150                   170                      190                  210
        .            .          .          .           .            .
CATGATGCTCTTCATAAGAACCACAAAGATGTCACAGACTCTTTTTATCCAGCAATGAGACTAATTCTTC
-+----|----+----|----+----|----+----|----+----|----+----|----+----|----
GTACTACGAGAAGTATTCTTGGTGTTTCTACAGTGTCTGAGAAAAATAGGTCGTTACTCTGATTAAGAAG
 H  D  A  L  H  K  N  H  K  D  V  T  D  S  F  Y  P  A  M  R  L  I  L  P 230                   250                      270
        .            .          .          .           .            .
CTCAGCTTAGAAAGAGAGAGAATGGCCTATGGAATTAAAGAAACTATGCTTGCTAAGCTTTATATTGAGTT
-+----|----+----|----+----|----+----|----+----|----+----|----+----|----
GAGTCGATCTTTCTCTCTCTTACCGGATACCTTAATTTCTTTGATACGAACGATTCGAAATATAACTCAA
 Q  L  E  R  E  R  M  A  Y  G  I  K  E  T  M  L  A  K  L  Y  I  E  L
```

Figure 1C

```
                290                310                330                350
                  .                  .                  .                  .
        GCTTAATTTACCTAGAGATGGAAAAGATGCCCTCAAACTTTTAAACTACAGAACACCCACTGGAACTCAT
        -+----------+----------+----------+----------+----------+----------+-
        CGAATTAAATGGATCTCTACCTTTTCTACGGGAGTTTGAAAATTGATGTCTTGTGGGTGACCTTGAGTA
         L  N  L  P  R  D  G  K  D  A  L  K  L  L  N  Y  R  T  P  T  G  T  H
                370                390                410
                  .                  .                  .
        GGAGATGCTGGAGACTTTGCAATGATTGCATATTTTGTGTTGAAGCCAAGATGTTTACAGAAAGGAAGTT
        -+----------+----------+----------+----------+----------+----------+-
        CCTCTACGACCTCTGAAACGTTACTAACGTATAAAACACAACTTCGGTTCTACAAATGTCTTTCCTTCAA
         G  D  A  G  D  F  A  M  I  A  Y  F  V  L  K  P  R  C  L  Q  K  G  S  L
                430                450                470                490
                  .                  .                  .                  .
        TAACCATACAGCAAGTAAACGACCTTTTAGACTCAATTGCCAGCAATAATTCTGCTAAAAGAAAAGACCT
        -+----------+----------+----------+----------+----------+----------+-
        ATTGGTATGTCGTTCATTTGCTGGAAAATCTGAGTTAACGGTCGTTATTAAGACGATTTTCTTTTCTGGA
         T  I  Q  Q  V  N  D  L  L  D  S  I  A  S  N  N  S  A  K  R  K  D  L
                510                530                550
                  .                  .                  .
        AATAAAAAGAGCCTTCTTCAACTTATAACTCAGAGTTCAGAGCAAAAGTGGCTTATACGGATG
        -+----------+----------+----------+----------+----------+----------+-
        TTATTTTTCTCGGAAGAAGTTGAATATTGAGTCTCAAGTCGTGAACTCGTTTCACCGAATATGCCTAC
         I  K  S  L  L  Q  L  I  T  Q  S  S  A  L  E  Q  K  W  L  I  R  M
```

Figure 1D

```
        570                590                610                630
          .                  .                  .                  .
ATCATAAAGGATTTAAAGCTTGGTGTTAGTCAGCAAACTATCTTTTCTGTTTTCATAATGATGCTGCTG
--+---------+---------+---------+---------+---------+---------+
TAGTATTTCCTAAATTTCGAACCACAATCAGTCGTTGATAGAAAAGACAAAAGTATTACTACGACGAC
 I  I  K  D  L  K  L  G  V  S  Q  Q  T  I  F  S  V  F  H  N  D  A  A  E 650                670                690
                  .                  .                  .
AGTTGCATAATGTCACTACAGATCTGGAAAAGTCTGTAGGCAACTGCATGATCCTTCTGTAGGACTCAG
--+---------+---------+---------+---------+---------+---------+
TCAACGTATTACAGTGATGTCTAGACCTTTTCAGACATCCGTTGACGTACTAGGAAGACATCCTGAGTC
 L  H  N  V  T  T  D  L  E  K  V  C  R  Q  L  H  D  P  S  V  G  L  S 710                730                750                770
          .                  .                  .                  .
TGATATTTCTATCACTTTATTTTCTGCATCAAAACCAATGCTAGCTGCTATTGCAGATATTGAGCACATT
--+---------+---------+---------+---------+---------+---------+
ACTATAAAGATAGTGAAATAAAAGACGTAGTTTTGGTTACGATCGACGATAACGTCTATAACTCGTGTAA
 D  I  S  I  T  L  F  S  A  S  K  P  M  L  A  A  I  A  D  I  E  H  I 790                810                830
                  .                  .                  .
GAGAAGGATATGAAACATCAGAGTTTCTACATAGAAACCAAGCTAGATGGTGAACGTATGCAAATGCACA
--+---------+---------+---------+---------+---------+---------+
CTCTTCCTATACTTTGTAGTCTCAAAGATGTATCTTTGGTTCGATCTACCACTTGCATACGTTTACGTGT
 E  K  D  M  K  H  Q  S  F  Y  I  E  T  K  L  D  G  E  R  M  Q  M  H  K
```

Figure 1E

```
          850              870              890              910
            .                .                .                .
AAGATGGAGATGTATATAAATACTTCTCTCGAAATGGATATAACTACACTGATCAGTTTGGTGCTTCTCC
--+--------+--------+--------+--------+--------+--------+--------+---
TTCTACCTCTACATATATTTATGAAGAGAGCTTTACCTATATTGATGTGACTAGTCAAACCACGAAGAGG
 D  D  V  Y  K  Y  F  S  R  N  G  Y  N  Y  T  D  Q  F  G  A  S  P 930              950              970
            .                .                .
TACTGAAGGTTCTCTCTTACCCCATTCATTCATAATGCATTCAAAGCAGATATACAAATCTGTATTCTTGAT
--+--------+--------+--------+--------+--------+--------+--------+-----
ATGACTTCCAAGAGAATGGGGTAAGTAAGTATTACGTAAGTTTCGTCTATATGTTTAGACATAAGAACTA
 T  E  G  S  L  T  P  F  I  H  N  A  F  K  A  D  I  Q  I  C  I  L  D 990              1010             1030             1050
            .                .                .                .
GGTGAGATGATGGCCTATAATCCTAATACACAAACTTTCATGCAAAAGGGAACTAAGTTTGATATTAAAA
--+--------+--------+--------+--------+--------+--------+--------+---
CCACTCTACTACCGGATATTAGGATTATGTGTTTGAAAGTACGTTTTCCCTTGATTCAAACTATAATTTT
 G  E  M  M  A  Y  N  P  N  T  Q  T  F  M  Q  K  G  T  K  F  D  I  K  R 1070             1090             1110
            .                .                .
GAATGGTAGAGGATTCTGATCTGCAAACTTGTTATTGTGTTTTTGATGTATTGATGGTTAATAATAAAAA
--+--------+--------+--------+--------+--------+--------+--------+---
CTTACCATCTCCTAAGACTAGACGTTTGAACAATAACACAAAAACTACATAACTACCAATTATTATTTT
 M  V  E  D  S  D  L  Q  T  C  Y  C  V  F  D  V  L  M  V  N  N  K  K
```

Figure 1F

```
                                  1170                        1190
     1130              1150         .                           .
       .                 .          |                           |
GCTAGGGCATGAGACTCTGAGAAAGAGGTATGAGATTCTTAGTAGTATTTTTACACCAATTCCAGGTAGA
-+---------+---------+---------+---------+---------+---------+---------
CGATCCCGTACTCTGAGACTCTTTCTCCATACTCTAAGAATCATCATAAAAATGTGGTTAAGGTCCATCT
   L  G  H  E  T  L  R  K  R  Y  E  I  L  S  S  I  F  T  P  I  P  G  R 1230                        1250
                1210                .                           .
                  .                 |                           |
ATAGAAATAGTGCAGAAAACACAAGCTCATACTAAGAATGAAGTAATTGATGCATTGAATGAAGCAATAG
-+---------+---------+---------+---------+---------+---------+---------
TATCTTTATCACGTCTTTTGTGTTCGAGTATGATGATTCTTACTTCATTAACTACGTAACTTACTTCGTTATC
   I  E  I  V  Q  K  T  Q  A  H  T  K  N  E  V  I  D  A  L  N  E  A  I  D 1310                        1330
                1270                .                           .
                  .                 |                           |
ATAAAAGAGAAGAGGGAATTATGGTAAAACAACCTCTATCCATCTACAAGCCAGACAAAGAGGTGAAGG
-+---------+---------+---------+---------+---------+---------+---------
TATTTTCTCTTCTCCCTTAATACCATTTTGTTGGAGATAGGTAGATGTTCGGTCTGTTTCTCCACTTCC
   K  R  E  E  G  I  M  V  K  Q  P  L  S  I  Y  K  P  D  K  R  G  E  G 1370                        1390
                1350                .                           .
                  .                 |                           |
GTGGTTAAAAATTAAACCAGAGTATGTCAGTGGACTAATGGATGAATTGGACATTTAATTGTTGGAGGA
-+---------+---------+---------+---------+---------+---------+---------
CACCAATTTTTAATTGGTCTCATACAGTCACCTGATTACCTACTTAACCTGTAAAATTAACAACCTCCT
   W  L  K  I  K  P  E  Y  V  S  G  L  M  D  E  L  D  I  L  I  V  G  G
```

Figure 1G

```
                1410                    1430                    1450                    1470
                   .                       .                       .                       .
       TATTGGGGTAAAGGATCACGGGGTGGAATGATGTCTCATTTTCTGTGTGCAGTAGCAGAGAAGCCCCTC
       ---+---------+---------+---------+---------+---------+---------+---
       ATAACCCCATTTCCTAGTGCCCCACCTTACTACAGAGTAAAAGACACACGTCATCGTCTCTTCGGGGAG
        Y  W  G  K  G  S  R  G  G  M  M  S  H  F  L  C  A  V  A  E  K  P  P  P 1490                    1510                    1530
                               .                       .                       .
       CTGGTGAGAAGCCATCTGTGTTTCATACTCTCTCGTGTTGGGTCTGGCTGCACCATGAAAGAACTGTA
       ---+---------+---------+---------+---------+---------+---------+---
       GACCACTCTTCGGTAGACACAAAGTATGAGAGAGCACAACCCAGACCGACGTGGTACTTTCTTGACAT
        G  E  K  P  S  V  F  H  T  L  S  R  V  G  S  G  C  T  M  K  E  L  Y 1550                    1570                    1590                    1610
                   .                       .                       .                       .
       TGATCTGGGTTTGAAATTGGCAAGTATTGGAAGCCTTTTCATAGAAAAGCTCCACCAAGCAGCAGCATTTA
       ---+---------+---------+---------+---------+---------+---------+---
       ACTAGACCCAAACTTTAACCGTTCATAACCTTCGGAAAAGTATCTTTTCGAGGTGGTTCGTCGTAAAT
        D  L  G  L  K  L  A  K  Y  W  K  P  F  H  R  K  A  P  P  S  S  I  L 1630                    1650                    1670
                               .                       .                       .
       TGTGGAACAGAGAAGCCAGAAGTATACATTGAACCTTGTAATTCTGTCATTGTTCAGATTAAAGCAGCAG
       ---+---------+---------+---------+---------+---------+---------+---
       ACACCTTGTCTCTTCGGTCTTCATATGTAACTTGGAACATTAAGACAGTAACAAGTCTAATTTCGTCGTC
        C  G  T  E  K  P  E  V  Y  I  E  P  C  N  S  V  I  V  Q  I  K  A  A  E
```

Figure 1I

```
                1970            1990           2010            2030
                   .               .              .               .
         TAATATATATTTGAAGATGTAGAGTTTTGTGTTATGAGTGGAACAGATAGCCAGCCAAAGCCTGACCTGGAG
         ---+---------+---------+---------+---------+---------+---------+
         ATTATATAAACTTCTACATCTCAAAACACAATACTCACCTTGTCTATCGGTCGTTTCGGACTGGACCTC
          N  I  F  E  D  V  E  F  C  V  M  S  G  T  D  S  Q  P  K  P  D  L  E 2050           2070            2090
                                  .              .               .
         AACAGAATTGCAGAATTTGGTGGTTATATAGTACAAAATCCAGGCCCAGACACGTACTGTGTAATTGCAG
         ---+---------+---------+---------+---------+---------+---------+
         TTGTCTTAACGTCTTAAACCACCAATATATCATGTTTTAGGTCCGGGTCTGTGCATGACACATTAACGTC
          N  R  I  A  E  F  G  G  Y  I  V  Q  N  P  G  P  D  T  Y  C  V  I  A  G 2110           2130           2150            2170
                    .              .              .               .
         GGTCTGAGAACATCAGAGTGAAAATAAATTTGTCAAATAAACATGATGTTGTCAAGCCTGCATGGCT
         ---+---------+---------+---------+---------+---------+---------+
         CCAGACTCTTGTAGTCTCACTTTTATTTAAACAGTTTATTTGTACTACAACAGTTCGGACGTACCGA
          S  E  N  I  R  V  K  N  I  I  L  S  N  K  H  D  V  V  K  P  A  W  L 2190           2210            2230
                                  .              .               .
         TTTAGAATGTTTTAAGACCAAAAAGCTTTGTGTACCATGGCAGCCTCGCTTTATGATTCATATGTGCCCATCA
         ---+---------+---------+---------+---------+---------+---------+
         AAATCTTACAAAATTCTGGTTTTCGAAACATGGTACCGTCGGAGCGAAATACTAAGTATACACGGGTAGT
          L  E  C  F  K  T  K  S  F  V  P  W  Q  P  R  F  M  I  H  M  C  P  S
```

Figure 1J

```
         2250                2270                2290                2310
           .                   .                   .                   .
ACCAAAGAACATTTGCCCGTGAATATGATTGCTATGGTGATAGTTATTTCATTGATACAGACTTGAACC
-+-------+---------+---------+---------+---------+---------+---------+
TGGTTTCTTGTAAAACGGGCACTTATACTAACGATACCACTATCAATAAAGTAACTATGTCTGAACTTGG
 T  K  E  H  F  A  R  E  Y  D  C  Y  G  D  S  Y  F  I  D  T  D  L  N  Q 2330                2350                2370
                       .                   .                   .
AACTGAAGGAAGTATTCTCAGGAATTAAAAATTCTAACGAGCAGACTCCTGAAGAAATGGCTTCTCTGAT
-+---------+---------+---------+---------+---------+---------+--------
TTGACTTCCTTCATAAGAGTCCTTAATTTTTAAGATTGCTCGTCTGAGGACTTCTTTACCGAAGAGACTA
 L  K  E  V  F  S  G  I  K  N  S  N  E  Q  T  P  E  E  M  A  S  L  I 2390                2410                2430                2450
           .                   .                   .                   .
TGCTGATTAGAATATCGGTATTCCCTGGGATTGCTCCTCCTCAGTATGTTTCGACGCCACACCGTTTAT
-+---------+---------+---------+---------+---------+---------+--------+
ACGACTAAATCTTATAGCCATAAGGACCCTAACGAGAGGAGAGTCATACAAAGCTGCGGTGTGCAAATA
 A  D  L  E  Y  R  Y  S  W  D  C  S  P  L  S  M  F  R  R  H  T  V  Y 2470                2490                2510
                       .                   .                   .
TTGGACTCGTATGCTGTTATTAATGACCTGAGTACCAAAAATGAGGGGACAAGGTTAGCTATTAAAGCCT
-+---------+---------+---------+---------+---------+---------+---------
AACCTGAGCATACGACAATAATTACTGGACTCATGGTTTTTACTCCCCTGTTCCAATCGATAATTTCGGA
 L  D  S  Y  A  V  I  N  D  L  S  T  K  N  E  G  T  R  L  A  I  K  A  L
```

Figure 1K

```
          2530                 2550                2570              2590
             .                    .                   .                 .
TGGAGCTTCGGTTTCATGGAGCAAAAGTAGTTTCTTGTTTAGCTGAGGGAGTGTCTCATGTAATAATTGG
--+---------+---------+---------+---------+---------+---------+-------
ACCTCGAAGCCAAAGTACCTCGTTTTCATCAAAGAACAAATCGACTCCCTCACAGAGTACATTATTAACC
   E  L  R  F  H  G  A  K  V  V  S  C  L  A  E  G  V  S  H  V  I  I  G 2610                 2630                2650
                      .                    .                   .
GGAAGATCATAGTCGTGTTGCAGATTTTAAAGCTTTTAGAAGAACTTTTAAGAGAAAGTTTAAAATCCTA
--+---------+---------+---------+---------+---------+---------+-------
CCTTCTAGTATCAGCACAACGTCTAAAATTTCGAAAATCTTCTTGAAAATTCTCTTTCAAATTTTAGAT
   E  D  H  S  R  V  A  D  F  K  A  F  R  R  T  F  K  R  K  F  K  I  L 2670                 2690                2710              2730
             .                    .                   .                 .
AAAGAAAAGTTGGGTAACTGATTCAATTACAAGAAGAAAACCAGTATTTGATTTAAA
--+---------+---------+---------+---------+---------+---------+-------
TTTCTTTTCAACCCATTGACTAAGTTATCTGTTCACACTTAAATGTTCTTCTTTTGGTCATAAACTAAATTT
   K  E  S  W  V  T  D  S  I  D  K  C  E  L  Q  E  E  N  Q  Y  L  I  *

2750                 2770                2790
                      .                    .                   .
GCTAGGTTTCCTAGTGAGGAAAGCCCTCTGATCTGGCAGACTCATTGCAGCAGGTGGTAATGATAAATAC
--+---------+---------+---------+---------+---------+---------+-------
CGATCCAAAGGATCACTCCTTTCGGAGACTAGACCGTCTGAGTAACGTCGTCCACCATTACTATTTTATG
```

Figure 1L

```
                           2830                 2850                 2870
        2810                 .                    .                    .
          .
TAAACTACATTTTTATTTTTGTATCTTAAAAAATCTATGCCTAAAAAGTATCATTACATATAGGAAAACAAT
--+---------+---------+---------+---------+---------+---------+
ATTTGATGTAAAAATAATAAAACATAGAATTTTTAGATACGGATTTTTCATAGTAATGTATATCCTTTGTTA 2890                 2910                 2930
                             .                    .                    .
AATTTTAACTTTTTAAGGTTGAAAAAGACAATAGCCCAAGCCCAAGAAAGAAAAATTATCTTGAATGTAGTA
--+---------+---------+---------+---------+---------+---------+
TTAAAATTGAAAATTCCAACTTTTCTGTTATCGGGTTTCGGTTCTTTCTTTTTAATAGAACTTACATCAT 2950                 2970                 2990                 3010
                             .                    .                    .                    .
TTCAATGATTTTTATGATCAAGGTGAAATAACAGTCTAAAGAAGAGGTGTTTTTATATATCCATATA
--+---------+---------+---------+---------+---------+---------+
AAGTTACTAAAAATACTAGTTCCACTTTATTTGTCAGATTTCTTCTCCACAAAAATATTATAGGTATAT 3030                 3050
                             .                    .
GAAATCTAGAATTTTTACTTAGATACTAATAAAAT
--+---------+---------+
CTTTAGATCTTAAAAATGAATCTATGATTATTTTA
```

Figure 2A

```
275 PVEDACWKPGQKVPYLAVARTFEKIEEVSARLRMVETLSNLLRSVVALSP 324
  2 AASQTSQTVASHVPFADLCSTLERIQKSKGRAEKIRHFREFLDSWRKFHD  51

325 P..........................DLLPVLYLSLNHLGPPQQGLELGVGDGVLLK............ 356
 52 ALHKNHKDVTDSFYPAMRLILPQLE..RERMAYGIKETMLAKLYIELLNL  99

357 AVAQATGRQLESVRAEAAEKGDVGLVAENSRSTQRLMLPPPPL.TASGVF 405
100 PRDGKDALKLLNYRTPTGTHGDAGDFAM....IAYFVLKPRCLQKGSLTI 145

406 SKFRDIARLTGSASTAKKIDIIK.....GLFVACRHSEARFIARSLSGRLR 451
146 QQVNDLLDSIASNNSAKRKDLIKKSLLQLITQSSALEQKWLIRMIIKDLK 195

452 LGLAEQSVLAALSQAVSLTPPGQEFPPAMVDAGKGKTAEARKTWLEEQGM 501
196 LGVSQQTIFSVF...................HNDAAELHNV........ 217
```

Figure 2B

```
502  ILKQTFCEVPDLDRIIPVLLEHGLERLPEHCKLSPGIPLKPMLAHPTRGI  551
218  .......TTDLEKVCRQLHDPSVGLSDISITLFSAS..KPMLA.AIADI  256

552  SEVLKRFEEAAFTCEYKYDGQRAQIHALEGGEVKIFSRNQEDNTGKYPD.  600
257  EHIEKDMKHQSFYIETKLDGERMQMHK.DGDVYKYFSRNGYNYTDQFGAS  305

601  ......IISRIPKIKLPSVTSFILDTEAVAWDREKKQIQPFQVLTTRKRKE  645
306  PTEGSLTPFIHNAFKADIQICILDGEMMAYNPN...TQTFMQKGTKFDIK  352

646  VDASEIQVQVCLYAFDLIYLNGESLVREPLSRRRQLLRENFVETEGEFVF  695
353  RMVEDSDLQTCYCVFDVLMVNNKKLGHETLRKRYEILSSIFTPIPGRIEI  402

696  ATSLDTKDIEQIAEFLEQSVKDSCEGLMVKTLDVDATYEIAKRSHNWLKL  745
403  VQKTQAHTKNEVIDALNEAIDKREEGIMVK..QPLSIYKPDKRGEGWLKI  450
```

Figure 2C

```
746 KKDYLDGVGDTLDLVVIGAYLGRGKRAGRYGGFLLASYD......EDSEEL 790
451 KPEYVSGLMDELDILIVGGYWGKGSRGGMMSHFLCAVAEKPPPGEKPSVF 500
791 QAICKLGTGFSDEELEEHHQSLKALVLPSPR....PYVRIDGAVIPDHWLD 837
501 HTLSRVGSGCTMKELYDLGLKLAKYWKPFHRKAPPSSILCGTEKPEVYIE 550
838 P..SAVWEVKCADLSLSPIYPAARGLVDSDKGISLRFPRFIRVREDKQPE 885
551 PCNSVIVQIKAAEIVPSDMY..........KTGCTLRFPRIEKIRDDKEWH 591
886 QATTSAQVACLYRKQSQIQNQQGEDSGSDPED 917
592 ECMTLDDLEQLRGKASGKLASKHLYIGGDDEP 623
```

HUMAN DNA LIGASE IV

This is a Continuation-in-Part Application of PCT/US94/12922, filed Nov. 8, 1994, which is entitled to priority under 35 U.S.C. §120.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is Human DNA Ligase IV. The invention also relates to inhibiting the action of such polypeptides.

DNA strand interruptions and gaps are generated during replication, repair and recombination. In mammalian cell nuclei, rejoining of such breaks depends on several different DNA polymerases and DNA ligases. The occurrence of three different DNA ligases was established previously by biochemical and immunological characterization of purified enzymes (Tomkinson, A. E., et al., J. Biol. Chem., 266:21728–21735 (1991)). DNA ligases are enzymes that catalyze DNA replication, excision repair and recombinational repair in mammalian cells (Li, J. J. and Kelly, T. J., PNAS, USA, 81:6973–77 (1984) and Wook, R. O. et al., Cell, 53:97–106 (1988)). In bacteria, three DNA ligases, namely DNA Ligase I, DNA Ligase II and DNA Ligase III have been discovered, while in humans all three have been found but only DNA Ligase I has been cloned.

A full-length human cDNA encoding DNA Ligase I has been obtained by functional complementation of a S. cereviasiae cdc9 temperature-sensitive DNA ligase mutant (Barker, D. G., Eur. J. Biochem., 162:659–67 (1987)). The full-length cDNA encodes a 102-kDa protein of 919 amino acid residues. There is no marked sequence homology to other known proteins except for microbial DNA ligases. The active site lysine residue is located at position 568. DNA Ligase I requires magnesium and ATP for activity. The main function of DNA Ligase I is the joining of Okazaki fragments during lagging-strand DNA replication. It also effectively seals single-strand breaks in DNA and joins restriction enzyme DNA fragments with staggered ends. The enzyme is also able to catalyze blunt-end joining of DNA. DNA Ligase I can join oligo (dT) molecules hydrogen-bonded to poly (dA), but the enzyme differs from T4 DNA Ligase in being unable to ligate oligo (dT) with a poly (rA) complementary strand.

Human DNA Ligase II is more firmly associated with the cell nuclei. This enzyme is a labile protein, which is rapidly inactivated at 42° C. DNA Ligase II resembles other eukaryotic DNA Ligases in requiring ATP as cofactor, but the enzyme differs from DNA Ligase I in having a much higher association for ATP. DNA Ligase II catalyzes the formation of phosphodiester bonds with an oligo (dT).poly (rA) substrate, but not with an oligo (rA).poly (dT) substrate, so it differs completely from DNA Ligase I in this regard (Arrand, J. E. et al., J. Biol. Chem., 261:9079–82 (1986)).

A recently detected enzyme, which is larger than DNA Ligase II and apparently unrelated to that protein, has been named DNA-Ligase III (Tomkinson, A. E. et al., J. Biol. Chem., 266:21728–35 (1991)). DNA Ligase III resembles DNA Ligase I, and differs from DNA Ligase II, in binding only weakly to hydroxylapatite in having a low affinity, for ATP. DNA Ligase I and III however are not closely related. DNA Ligase III repairs single strand breaks in DNA efficiently, but it is unable to perform either blunt-end joining or AMP-dependent relaxation of supercoiled DNA (Elder, R. H. et al., Eur. J. Biochem., 203:53–58 (1992)).

The mechanism for joining of DNA strand interruptions by DNA ligases has been widely described. The reaction is initiated by the formation of a covalent enzyme-adenylate complex. Mammalian and viral DNA ligases employ ATP as cofactor, whereas bacterial DNA ligases use NAD to generate the adenylyl group. The ATP is cleaved to AMP and pyrophosphate with the adenylyl residue linked by a phosphoramidate bond to the ε-amino group of a specific lysine residue at the active site of the protein (Gumport, R. I., et al.., PNAS, 68:2559–63 (1971)). Reactivated AMP residue of the DNA ligase-adenylate intermediate is transferred to the 5' phosphate terminus of a single strand break in double stranded DNA to generate a covalent DNA-AMP complex with a 5'—5' phosphoanhydride bond. This reaction intermediate has also been isolated for microbial and mammalian DNA ligases, but is more short lived than the adenylylated enzyme. In the final step of DNA ligation, unadenylylated. DNA ligases required for the generation of a phosphodiester bond catalyzes displacement of the AMP residue through attack by the adjacent 3'-hydroxyl group on the adenylylated site.

The polypeptide of the present invention has been putatively identified as a human DNA Ligase IV as a result of amino acid sequence homology.

In accordance with one aspect of the present invention, there are provided novel mature polypeptides which are human DNA Ligase IV, as well as biologically active and diagnostically or therapeutically useful fragments, analogs and derivatives thereof.

In accordance with another aspect of the present invention, there are provided isolated nucleic acid molecules encoding human DNA Ligase IV, including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptides by recombinant techniques comprising culturing recombinant prokaryotic and/or eukaryotic host cells, containing a human DNA Ligase IV nucleic acid sequence, under conditions promoting expression of said protein and subsequent recovery of said protein.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

In accordance with another aspect of the present invention there is provided a method of treating conditions which are related to insufficient human DNA Ligase IV activity via gene therapy comprising inserting the DNA Ligase IV gene into a patient's cells either in vivo or ex vivo. The gene is expressed in transduced cells and as a result, the protein encoded by the gene may be used therapeutically, for example, to prevent disorders associated with defects in DNA, for example, abnormal cellular proliferation, for example tumors, to treat severe immunosuppression, stunted growth and lymphoma, as well as cellular hypersensitivity to DNA-damaging agents.

In accordance with yet a further aspect of the present invention, there is also provided nucleic acid probes comprising nucleic acid molecules of sufficient length to specifically hybridize to human sequences which may be used diagnostically to detect a mutation in the gene encoding DNA Ligase IV.

In accordance with yet another aspect of the present invention, there are provided antagonists to such polypeptides, which may be manufactured intracellularly or administered through gene therapy to inhibit the action of such polypeptides, for example, to target and destroy undesired cells, e.g., cancer cells.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. (1A–1L) shows the cDNA sequence (SEQ ID NO:1) and the corresponding deduced amino sequence (SEQ ID NO:2) of the DNA Ligase IV polypeptide. The standard one letter abbreviation for amino acids is used.

Figure 1H:
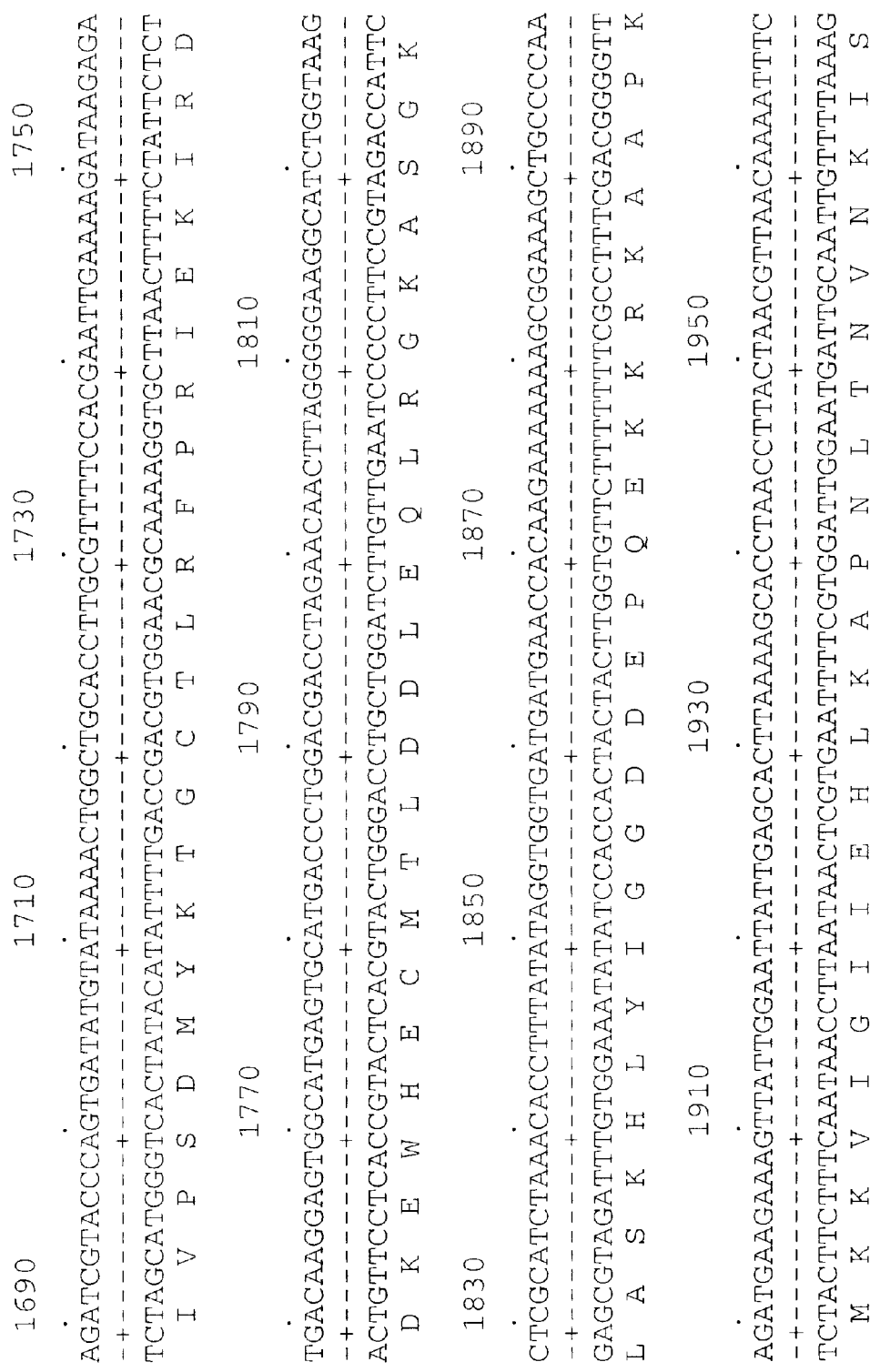

FIG. (2A–2C) illustrates the amino acid homology between human DNA Ligase I (upper line HLIG1) (SEQ ID NO:9) and human DNA Ligase IV (lower line HLIG4).

In accordance with an aspect of the present invention, there is provided an isolated nucleic acid (polynucleotide) which encodes for the mature polypeptide having the deduced amino acid sequence of FIG. 1 or for the mature polypeptide encoded by the cDNA of the clone deposited as ATCC Deposit No. 75880 on Aug. 31, 1994. This deposit is a biological deposit with the ATCC, 10801 University Boulevard, Manassas, Va. 20110-2209. Since the strain referred to is being maintained under the terms of the Budapest Treaty, it will be made available to a patent office signatory to the Budapest Treaty.

A polynucleotide encoding a polypeptide of the present invention may be obtained from testis, thymus and heart. The polynucleotide of this invention was discovered in a cDNA library derived from human activated T-cells. It is structurally related to the DNA ligase family. It contains an open reading frame encoding a protein of 911 amino acid residues. The protein exhibits the highest degree of homology to rabbit DNA ligase with 29% identity and 51% similarity over a the entire protein. It is also important that there is a conserved active lysine residue which is bordered on either side by a hydrophobic amino acid residue, and the sequence E-KYDG-R is common to enzymes from different sources such as mammalian cells, yeasts, vaccinia virus and bacteriophage T7.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 or that of the deposited clone or may be a different coding sequence which coding sequence, as a result of the redundancy or degeneracy of the genetic code, encodes the same mature polypeptide as the DNA of FIG. 1 or the deposited cDNA.

The polynucleotide which encodes for the mature polypeptide of FIG. 1 or for the mature polypeptide encoded by the deposited cDNA may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or the same mature polypeptide encoded by the cDNA of the deposited clone as well as variants of such polynucleotides which variants encode for a fragment, derivative or analog of the polypeptide of FIG. 1 or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the-deposited materials, and no such license is hereby granted.

The present invention further relates to a DNA Ligase IV polypeptide which has the deduced amino acid sequence of FIG. 1 or which has the amino acid sequence encoded by the deposited cDNA, as well as fragments, analogs and derivatives of such-polypeptide.

The terms "fragment," "derivative" and "analog" when referring to the polypeptide of FIG. 1 or that encoded by the deposited cDNA, means a polypeptide which retains essentially the same biological function or activity as such polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, which is employed for purification of the mature polypeptide. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector The vector may be, for example, in the form of a plasmid, a viral particle, a phage, etc. The engineered host cells can be cultured in conventional nutrient media modified as appropriate for activating promoters, selecting transformants or amplifying the DNA Ligase IV genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequences) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1,pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The DNA Ligase IV polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The DNA Ligase IV polypeptides and agonists and antagonists which are polypeptides, described below, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Once the DNA Ligase IV polypeptide is being expressed intra-cellularly via gene therapy, it may be used to repair single-strand breaks in DNA which result from DNA-damaging agents, e.g., UV radiation. Several human syndromes result from autosomal recessive inheritance for the DNA ligase gene. These syndromes cause severe immunodeficiency and greatly increases the susceptibility of abnormal cellular differentiation due to the disrepair of DNA while at the cellular level they are characterized by chromosome instability and hypersensitivity to DNA-damaging agents. These syndromes include Fanconi's anemia and Blackfan-diamond anemia.

The polypeptide of the present invention may also be employed to treat severe immunosuppression which is the result of a defect in the DNA ligase III gene and stunted growth and lymphoma which results from defective rejoining of DNA.

Similarly, the polynucleotide of the present invention is also useful for identifying other molecules which have similar biological activity. An example of a screen for this is isolating the coding region of the DNA Ligase IV gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The polypeptide and/or polynucleotide of the present invention may also be employed in relation to scientific research, synthesis of DNA and for the manufacture of DNA vectors. The polypeptide and/or polynucleotide of the present invention may be sold into the research market. Thus, for example DNA Ligase IV may be used for ligation of DNA sequences in vitro in a manner similar to other DNA ligases of the art.

This invention also provides a method of screening compounds to identify those which enhance (agonists) or block (antagonists) the DNA-joining reaction catalyzed by human DNA Ligase IV. An example of such method comprises combining ATP and DNA Ligase IV and DNA having single-strand breaks with the compound under conditions where the DNA ligase would normally cleave ATP to AMP and the AMP is transferred to the 5' phosphate terminus of a single strand break in double-stranded DNA to generate a covalent DNA-AMP complex with the single strand break being subsequently repaired. The DNA having the single-strand breaks may be supplied in the above example by mutant cells which are deficient in proteins that are responsible for strand break repair, for example mutant rodent cells deficient in XRCC1 and the cdc9 *S. Cerevisiae* DNA ligase mutant. The ability of the compound to enhance or block the catalysis of this reaction could then be measured to determine if the compound is an effective agonist or antagonist.

Human DNA Ligase IV is produced and functions intra-cellulary, therefore, any antagonists must be intra-cellular. Potential antagonists to human DNA Ligase IV include antibodies which are produced intra-cellularly. For example, an antibody identified as antagonizing DNA Ligase IV may be produced intra-cellularly as a single chain antibody by procedures known in the art, such as transforming the appropriate cells with DNA encoding the single chain antibody to prevent the function of human DNA Ligase IV.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of DNA Ligase IV. The antisense RNA oligonucleotide hybridizes to the mRNA in vivo and blocks translation of the mRNA molecule into the DNA Ligase IV (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of DNA Ligase IV.

Yet another potential antagonist includes a mutated form, or mutein, of DNA Ligase IV which recognizes DNA but does not repair single-strand breaks and, therefore, acts to prevent human DNA Ligase IV from functioning.

The antagonists may be employed to target undesired cells, e.g., cancer cells, since the prevention of DNA Ligase IV prevents repair of single-strand breaks in DNA and will eventually result in death of the cell.

The small molecule agonists and antagonists of the present invention may be employed in combination with a suitable pharmaceutical carrier. Such compositions comprise a therapeutically effective amount of the molecule and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

Fragments of the full length Human DNA Ligase IV gene may be used as a hybridization probe for a cDNA library to isolate the full length DNA Ligase IV gene and to isolate other genes which have a high sequence similarity to the DNA Ligase IV gene. Probes of this type can be, for example, 30, 40, 50 75, 90, 100 or 150 bases. Preferably, however, the probes have between 30 and 50 base pairs. The probe may also be used to identify a cDNA clone corresponding to a full length transcript and a genomic clone or clones that contain the complete gene including regulatory and promotor regions, exons, and introns. The probe may be labelled, for example, by radioactivity to facilitate identification of hybridization.

This invention also provides the use of the human DNA Ligase IV gene as a diagnostic. For example, some diseases result from inherited defective genes. These genes can be detected by comparing the sequence of the defective gene with that of a normal one. That is, a mutant gene would be associated with hypersensitivity to DNA-damaging agents and an elevated susceptibility to abnormal cell growth, for example tumors and cancer.

Individuals carrying mutations in the human DNA Ligase IV gene may be detected at the DNA level by a variety of techniques. Nucleic acids used for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986) prior to analysis. RNA or cDNA may also be used for the same purpose. Deletions or insertions can be detected by a change in size of the amplified product in comparison to the normal genotype. Point mutations can be identified by hybridizing amplified DNA to radiolabeled DNA Ligase IV RNA or alternatively, radiolabeled DNA Ligase IV antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing fornamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase protection and S1 protection or the chemical cleavage method (e.g., Cotton et al., PNAS, USA, 85:4397–4401 (1985)).

Thus, the detection of a specific DNA sequence may be achieved by method such as hybridization, RNase protection, chemical cleavage, direct DNA sequencing, or the use of restriction enzymes, e.g., restriction fragment length polymorphisms, and Southern blotting of genomic DNA. Also, mutations may be detected by in situ analysis.

In addition, some diseases are a result of, or are characterized by, changes in gene expression which can be detected by changes in the mRNA. Alternatively, the DNA Ligase IV gene can be used as a reference to identify individuals expressing a decreased level of DNA Ligase IV protein, e.g., by Northern blotting.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The gene of the present invention has been mapped to chromosome 13q33-34.

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of DNA Ligase IV

The DNA sequence encoding DNA Ligase IV, ATCC # 75880 is initially amplified using PCR oligonucleotide primers corresponding to the 5' sequences of the processed DNA Ligase IV protein. The 5' oligonucleotide primer has the sequence 5' GCG GGATCCATGAGACTAATTCTTCCTCAG 3' (SEQ ID NO:3) contains a Bam HI restriction enzyme site (underlined) followed by 21 nucleotides of DNA Ligase IV coding sequence starting from the presumed terminal amino acid of the processed protein codon. The 3' sequence 5' GCG CTGCAGTTAAATCAAATACTGGTTTTG 3' (SEQ ID NO:4) contains complementary sequences to a Pst I site (underlined) and is followed by 21 nucleotides of DNA Ligase IV at C-terminal of DNA Ligase IV. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with Bam HI and Pst I. The amplified sequences are ligated into pQE-9 and inserted in frame with the sequence encoding for the histidine tag and the RBS. The ligation mixture is then used to transform E. coli strain M15/rep 4 available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized protein extract is purified from this solution by chromatography on a Nickel-Chelate column under conditions that allow for tight binding by proteins containing the 6-His tag (Hochuli, E. et al., J. Chromatography 411:177–184 (1984)) and eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 2

Cloning and Expression of DNA Ligase IV Using the Baculovirus Expression System A DNA sequence encoding full length DNA Ligase IV protein, ATCC #75880, is amplified using PCR oligonucleotide primers corresponding to the 5' and 3' sequences of the gene:

The 5' primer has the sequence 5' GCGCCCGGG ATGAGACTAATT CTTCTCCAG 3' (SEQ ID NO:5) and contains a Sma I restriction enzyme site (in bold) followed first by 21 nucleotides resembling an efficient signal for the initiation of translation in eukaryotic cells (Kozak, M., J. Mol. Biol., 196:947–950, (1987)) (the initiation codon for translation "ATG" is underlined).

The 3' primer has the sequence 5' GCGGGTACCT-TAAATCAAATACTGGTTTTC 3' (SEQ ID NO:6) and contains the cleavage site for the restriction endonuclease Asp 718 (in bold) and 21 nucleotides complementary to the C-terminal sequence of the DNA Ligase IV gene. The amplified sequences were isolated from a 1% agarose gel using a commercially available kit ("Geneclean," BIO 101 Inc., La Jolla, Calif.). The fragment was then digested with the endonucleases Sma I and Asp 718 and then purified again on a 1% agarose gel. This fragment is designated F2.

The vector pRG1 (modification of pVL941 vector, discussed below) is used for the expression of the DNA Ligase IV protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases Sma I and Asp 718. The polyadenylation site of the simian virus (SV)40 is used for efficient polyadenylation. For an easy selection of recombinant viruses the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid is digested with the restriction enzymes Sma I and Asp 718 and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. E.coli HB101 cells are then transformed and bacteria identified that contained the plasmid (pBac DNA Ligase IV) with the DNA Ligase IV gene using the enzymes Sma I and Asp 718. The sequence of the cloned fragment is confirmed by DNA sequencing.

5 $\mu$g of the plasmid pBac DNA Ligase IV was cotransfected with 1.0 $\mu$g of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 $\mu$g of BaculoGold™ virus DNA and 5 $\mu$g of the plasmid pBac DNA Ligase IV are mixed in a sterile well of a microtiter plate containing 50 $\mu$l of serum free Grace's medium (Life Technologies Inc., Gaithersburg, Md.). Afterwards 10 $\mu$l Lipofectin plus 90 $\mu$l Grace's medium are added, mixed and incubated for 15 minutes at room temperature. Then the transfection mixture is added dropwise to the Sf9 insect cells (ATCC CRL 1711) seeded in a 35 mm tissue culture plate with 1 ml Grace' medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10) .

Four days after the serial dilution of the viruses is added to the cells, blue stained plaques are picked with the tip of an Eppendorf pipette. The agar containing the recombinant viruses is then resuspended in an Eppendorf tube containing 200 $\mu$l of Grace's medium. The agar is removed by a brief centrifugation and the supernatant containing the recombinant baculoviruses is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-DNA Ligase IV at a multiplicity of infection (MOI) of 2. Six hours later the medium is removed and replaced with SF900 II medium minus methionine and cysteine (Life Technologies Inc., Gaithersburg). 42 hours later 5 $\mu$Ci of $^{35}$S-methionine and 5 $\mu$Ci $^{35}$S cysteine (Amersham) are added. The cells are further incubated for 16 hours before they are harvested by centrifugation and the labelled proteins visualized by SDS-PAGE and autoradiography.

EXAMPLE 3

Expression of Recombinant DNA Ligase IV in COS Cells

The expression of plasmid, DNA Ligase IV HA is derived from a vector pcDNAI/Amp (Invitrogen) containing: 1) SV40 origin of replication, 2) ampicillin resistance gene, 3) E.coli replication origin, 4) CMV promoter followed by a polylinker region, a SV40 intron and polyadenylation site. A DNA fragment encoding the entire DNA Ligase IV precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, Cell 37:767 (1984)). The infusion of HA tag to our target protein allows easy detection of the recombinant protein with an antibody that recognizes the HA epitope.

The plasmid construction strategy is described as follows:

The DNA sequence encoding DNA Ligase IV, ATCC # 75880, is constructed by PCR on the original EST cloned using two primers: the 5' primer 5' GCG GAATTCATGAGACTAATTCTTCCTCAG 3' (SEQ ID NO:7) contains an Eco RI site (underlined) followed by 21 nucleotides of DNA Ligase IV coding sequence starting from the initiation codon; the 3' sequence 5'GCG CTCGAGTCAAGCGTAGTCTGGGACGTCGTATGGG TAAATCAAATACTGGTTTT GTTC 3' (SEQ ID N0:8) contains complementary sequences to an Xho I site (underlined), translation stop codon, HA tag and the last 21 nucleotides of the DNA Ligase IV coding sequence (not including the stop codon). Therefore, the PCR product contains an Eco RI site, DNA Ligase IV coding sequence followed by HA tag fused in frame, a translation termination stop codon next to the HA tag, and an Xho I site. The PCR amplified DNA fragment and the vector, pcDNAI/Amp, are digested with Eco RI and Xho I restriction enzyme and ligated. The ligation mixture is transformed into *E. coli* strain SURE (available from Stratagene Cloning Systems, 11099 North Torrey Pines Road, La Jolla, Calif. 92037) the transformed culture is plated on ampicillin media plates and resistant colonies are selected. Plasmid DNA is isolated from transformants and examined by restriction analysis for the presence of the correct fragment. For expression of the recombinant DNA Ligase IV, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the DNA Ligase IV HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 0.1% SDS, 1% NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 4

Expression Pattern of DNA Ligase IV in Human Tissue

Northern blot analysis may be performed to examine the levels of expression of DNA Ligase IV in human tissues. Total cellular RNA samples are isolated with RNAzol™ B system (Biotecx Laboratories, Inc. 6023 South Loop East, Houston, Tex. 77033). About 15 μg of total RNA isolated from each human tissue specified is separated on 1% agarose gel and blotted onto a nylon filter (Sambrook, Fritsch, and Maniatis, Molecular Cloning, Cold Spring Harbor Press, (1989)). The labeling reaction is done according to the Stratagene Prime-It kit with 50 ng DNA fragment. The labeled DNA is purified with a Select-G-50 column (5 Prime- 3 Prime, Inc. 5603 Arapahoe Road, Boulder, Colo. 80303). The filter containing the particular RNA blot is then hybridized with radioactive labeled full length DNA Ligase IV gene at 1,000,000 cpm/ml in 0.5 M NaPO$_4$, pH 7.4 and 7% SDS overnight at 65° C. After wash twice at room temperature and twice at 60° C. with 0.5×SSC, 0.1% SDS, the filter is then exposed at −70° C. overnight with an intensifying screen. 3).

EXAMPLE 5

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer $further includes a HindIII site. Equal quantities of the Moloney murine sarcoma virus linear backbone and the amplified $EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a nucleic acid sequence selected from the group consisting of:

(a) a nucleic acid sequence encoding the polypeptide set forth as amino acid residues 1 to 911 of SEQ ID NO:2;

(b) a nucleic acid sequence encoding the polypeptide set forth as amino acid residues 2 to 911 of SEQ ID NO:2;

(c) a nucleic acid sequence encoding the polypeptide set forth as amino acid residues 68 to 911 of SEQ ID NO:2;

(d) a nucleic acid sequence encoding a fragment of the polypeptide set forth as amino acid residues 1 to 911 of SEQ ID NO:2 wherein said fragment retains DNA ligase activity;

(e) a nucleic acid sequence encoding a fragment of the polypeptide set forth as amino acid residues 1 to 911 wherein said polypeptide contains at least one conservative amino acid substitution and further wherein said polypeptide retains DNA ligase activity;

(f) a nucleic acid sequence encoding at least 50 contiguous amino acid residues of SEQ ID NO:2;

(g) a nucleic acid sequence encoding at least 30 contiguous amino acid residues of SEQ ID NO:2;

(h) the nucleic acid sequence of a polynucleotide which hybridizes to a polynucleotide consisting of the complement of the nucleic acid sequence shown as SEQ ID NO:1 following incubation in 0.5 M NaPO$_4$, pH 7.4 and 7% SDS overnight at 65° C. and washing twice at 60° C. and twice at room temperature with 0.5×SSC and 0.1% SDS; and (i) a nucleic acid sequence complementary to the nucleic acid sequence of (a), (b), (c), (d), (e), (f), (g) or (h).

2. The isolated polynucleotide of claim 1 wherein the nucleic acid sequence is (g).

3. The isolated polynucleotide of claim 2 comprising a nucleic acid sequence which encodes at least 50 contiguous amino acids of SEQ ID NO:2.

4. The isolated polynucleotide of claim 3 comprising a nucleic acid sequence encoding amino acid residues 68 to 911 of SEQ ID NO:2.

5. The isolated polynucleotide of claim 4 comprising a nucleic acid sequence encoding amino acid residues 2 to 911 of SEQ ID NO:2.

6. The isolated polynucleotide of claim 5 comprising a nucleic acid sequence encoding amino acid residues 1 to 911 of SEQ ID NO:2.

7. The isolated polynucleotide of claim 1 wherein the nucleic acid sequence is (d).

8. The isolated polynucleotide of claim 1 wherein the nucleic acid sequence is (e).

9. The isolated polynucleotide of claim 1 wherein the nucleic acid sequence is (h).

10. The isolated polynucleotide of claim 1 wherein the nucleic acid sequence is (i).

11. The isolated polynucleotide of claim 1 wherein said polynucleotide is DNA and further wherein said nucleic acid sequence is (a), (b), (c), (d), (e), (f), (g) or (h).

12. A recombinant vector comprising the DNA of claim 11.

13. A recombinant host cell comprising the DNA of claim 11.

14. A polynucleotide comprising the DNA of claim 11 linked to a heterologous regulatory sequence which controls gene expression.

15. A process for producing a polypeptide comprising expressing from the host cell of claim 13 the encoded polypeptide and recovering said polypeptide.

16. The isolated polynucleotide of claim 6 comprising the nucleic acid sequence shown as nucleotides 1 to 2733 in SEQ ID NO:1.

17. The isolated polynucleotide of claim 1 consisting of a nucleic acid sequence selected from the group consisting of:
  (a) a nucleic acid sequence encoding the polypeptide set forth as amino acid residues 1 to 911 of SEQ ID NO:2;
  (b) a nucleic acid sequence encoding the polypeptide set forth as amino acid residues 2 to 911 of SEQ ID NO:2;
  (c) a nucleic acid sequence encoding the polypeptide set forth as amino acid residues 68 to 911 of SEQ ID NO:2;
  (d) a nucleic acid sequence encoding a fragment of the polypeptide set forth as amino acid residues 1 to 911 of SEQ ID NO:2 wherein said fragment retains DNA ligase activity;
  (e) a nucleic acid sequence encoding a fragment of the polypeptide set forth as amino acid residues 1 to 911 wherein said polypeptide contains at least one conservative amino acid substitution and further wherein said polypeptide retains DNA ligase activity;
  (f) a nucleic acid sequence encoding at least 50 contiguous amino acid residues of SEQ ID NO:2;
  (g) a nucleic acid sequence encoding at least 30 contiguous amino acid residues of SEQ ID NO:2; and
  (h) a nucleic acid sequence complementary to the nucleic acid sequence of (a), (b), (c), (d), (e), (f) or (g).

18. The isolated polynucleotide of claim 17 wherein the nucleic acid sequence is (a), (b), (c), (d), (e), (f) or (g).

19. The isolated polynucleotide of claim 18 fused to a heterologous polynucleotide.

20. The isolated polynucleotide of claim 19 wherein said polynucleotide is DNA.

21. A recombinant vector comprising the DNA of claim 20.

22. A recombinant host cell comprising the DNA of claim 20.

23. The isolated DNA of claim 20 linked to a regulatory sequence which controls gene expression.

24. A process for producing a polypeptide comprising expressing from the host cell of claim 22 the encoded polypeptide and recovering said polypeptide.

25. An isolated polynucleotide comprising a nucleic acid sequence selected from the group consisting of:
  (a) a nucleic acid sequence encoding the amino acid sequence of the polypeptide encoded by the human cDNA contained in ATCC Deposit No. 75880;
  (b) a nucleic acid sequence encoding the amino acid sequence of a fragment of the polypeptide encoded by the human cDNA contained in ATCC Deposit No. 75880 wherein said fragment retains DNA ligase activity;
  (c) a nucleic acid sequence encoding the amino acid sequence of a fragment of the polypeptide encoded by the human cDNA contained in ATCC Deposit No. 75880 wherein said amino acid sequence contains at least one conservative amino acid substitution and further wherein said fragment retains DNA ligase activity;
  (d) a nucleic acid sequence encoding at least 30 contiguous amino acids of the polypeptide encoded by the human cDNA contained in ATCC Deposit No. 75880;
  (e) a nucleic acid sequence encoding at least 50 contiguous amino acids of the polypeptide encoded by the human cDNA contained in ATCC Deposit No. 75880;
  (f) the nucleic acid sequence of a polynucleotide which hybridizes to the complement of the coding portion of the human cDNA contained in ATCC Deposit No. 75880 following incubation in 0.5 M $NaPO_4$, pH 7.4 and 7% SDS overnight at 65° C. and washing twice at 60° C. and twice at room temperature with 0.5×SSC and 0.1% SDS; and
  (g) a nucleic acid sequence complementary to the nucleic acid sequence of (a), (b), (c), (d), (e) or (f).

26. The isolated polynucleotide of claim 25 wherein said nucleic acid sequence is (d).

27. The isolated polynucleotide of claim 26 comprising a nucleic acid sequence encoding at least 50 contiguous amino acid residues of the polypeptide encoded by the human cDNA contained in ATCC Deposit No. 75880.

28. The isolated polynucleotide of claim 27 comprising a nucleic acid sequence encoding the polypeptide encoded by the human cDNA contained in ATCC Deposit No. 75880.

29. The isolated polynucleotide of claim 25 wherein said nucleic acid sequence is (b).

30. The isolated polynucleotide of claim 25 wherein said nucleic acid sequence is (c).

31. The isolated polynucleotide of claim 25 wherein said nucleic acid sequence is (f).

32. The isolated polynucleotide of claim 25 wherein said nucleic acid sequence is (g).

33. The isolated polynucleotide of claim 25 wherein said polynucleotide is DNA and further wherein said nucleic acid sequence is (a), (b), (c), (d), (e) or (f).

34. A recombinant vector comprising the DNA of claim 33.

35. A recombinant host cell comprising the DNA of claim 33.

36. The isolated DNA of claim 33 linked to regulatory sequence which controls gene expression.

37. A process for producing a polypeptide comprising expressing from the host cell of claim 35 the encoded polypeptide and recovering said polypeptide.

38. The isolated polynucleotide of claim 35 consisting of a nucleic acid sequence selected from the group consisting of:
(a) a nucleic acid sequence encoding the amino acid sequence of the polypeptide encoded by the human cDNA contained in ATCC Deposit No. 75880;
(b) a nucleic acid sequence encoding the amino acid sequence of a fragment of the polypeptide encoded by the human cDNA contained in ATCC Deposit No. 75880 wherein said fragment retains DNA ligase activity;
(c) a nucleic acid sequence encoding the amino acid sequence of a fragment of the polypeptide encoded by the human cDNA contained in ATCC Deposit No. 75880 wherein said amino acid sequence contains at least one conservative amino acid substitution and further wherein said fragment retains DNA ligase activity;
(d) a nucleic acid sequence encoding at least 30 contiguous amino acids of the polypeptide encoded by the human cDNA contained in ATCC Deposit No. 75880;
(e) a nucleic acid sequence encoding at least 50 contiguous amino acids of the polypeptide encoded by the human cDNA contained in ATCC Deposit No. 75880; and
(f) a nucleic acid sequence complementary to the nucleic acid sequence of (a), (b), (c), (d) or (e).

39. The isolated polynucleotide of claim 38 wherein the nucleic acid sequence is (a), (b), (c) (d) or (e).

40. The isolated polynucleotide of claim 39 fused to a heterologous polynucleotide.

41. The isolated polynucleotide of claim 40 fused to a polynucleotide which encodes a heterologous polypeptide.

42. The isolated polynucleotide of claim 40 wherein said polynucleotide is DNA.

43. A recombinant vector comprising the DNA of claim 42.

44. A recombinant host cell comprising the DNA of claim 42.

45. The isolated DNA of claim 42 linked to a regulatory sequence which controls gene expression.

46. A process for producing a polypeptide comprising expressing from the host cell of claim 44 the encoded polypeptide and recovering said polypeptide.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 3325 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 274..3006

(xi) SEQUENCE DESCRIPTION: SEQ ID NO:1:

```
CCACAGCGCT GTAGACTGCG CCGCATTAGA AGCCTGGCCT CCTGATGCTG TGCTCTTCAT        60

CTAGACCCAA GCCCCAGGTC GTGGGACGAT TTCTCCCGTT TTTGACTCCC TGGAACTGTA       120

TTGCCTGCTT TACCTGCGTA CATGTTGATT CTTTCTCATG GCAACCCCGC AGGAAACCAT       180

CAAGATCTCA TTTTACAGCT GGGATTCTCT GGTTCACAGA GGTAACGGAG CTTGCCCGAG       240

GCCAGTTAAA CGAGAAGATT CATCACCGCT TTG ATG GCT GCC TCA CAA ACT TCA        294
                                 Met Ala Ala Ser Gln Thr Ser
                                   1               5

CAA ACT GTT GCA TCT CAC GTT CCT TTT GCA GAT TTG TGT TCA ACT TTA        342
Gln Thr Val Ala Ser His Val Pro Phe Ala Asp Leu Cys Ser Thr Leu
         10              15                  20

GAA CGA ATA CAG AAA AGT AAA GGA CGT GCA GAA AAA ATC AGA CAC TTC        390
Glu Arg Ile Gln Lys Ser Lys Gly Arg Ala Glu Lys Ile Arg His Phe
     25                  30                  35

AGG GAA TTT TTA GAT TCT TGG AGA AAA TTT CAT GAT GCT CTT CAT AAG        438
Arg Glu Phe Leu Asp Ser Trp Arg Lys Phe His Asp Ala Leu His Lys
 40                  45                  50                  55

AAC CAC AAA GAT GTC ACA GAC TCT TTT TAT CCA GCA ATG AGA CTA ATT        486
Asn His Lys Asp Val Thr Asp Ser Phe Tyr Pro Ala Met Arg Leu Ile
                 60                  65                  70

CTT CCT CAG CTA GAA AGA GAG AGA ATG GCC TAT GGA ATT AAA GAA ACT        534
Leu Pro Gln Leu Glu Arg Glu Arg Met Ala Tyr Gly Ile Lys Glu Thr
             75                  80                  85

ATG CTT GCT AAG CTT TAT ATT GAG TTG CTT AAT TTA CCT AGA GAT GGA        582
Met Leu Ala Lys Leu Tyr Ile Glu Leu Leu Asn Leu Pro Arg Asp Gly
             90                  95                 100

AAA GAT GCC CTC AAA CTT TTA AAC TAC AGA ACA CCC ACT GGA ACT CAT        630
Lys Asp Ala Leu Lys Leu Leu Asn Tyr Arg Thr Pro Thr Gly Thr His
        105                 110                 115

GGA GAT GCT GGA GAC TTT GCA ATG ATT GCA TAT TTT GTG TTG AAG CCA        678
Gly Asp Ala Gly Asp Phe Ala Met Ile Ala Tyr Phe Val Leu Lys Pro
120                 125                 130                 135

AGA TGT TTA CAG AAA GGA AGT TTA ACC ATA CAG CAA GTA AAC GAC CTT        726
Arg Cys Leu Gln Lys Gly Ser Leu Thr Ile Gln Gln Val Asn Asp Leu
```

```
                    140                 145                 150
TTA GAC TCA ATT GCC AGC AAT AAT TCT GCT AAA AGA AAA GAC CTA ATA      774
Leu Asp Ser Ile Ala Ser Asn Asn Ser Ala Lys Arg Lys Asp Leu Ile
            155                 160                 165

AAA AAG AGC CTT CTT CAA CTT ATA ACT CAG AGT TCA GCA CTT GAG CAA      822
Lys Lys Ser Leu Leu Gln Leu Ile Thr Gln Ser Ser Ala Leu Glu Gln
        170                 175                 180

AAG TGG CTT ATA CGG ATG ATC ATA AAG GAT TTA AAG CTT GGT GTT AGT      870
Lys Trp Leu Ile Arg Met Ile Ile Lys Asp Leu Lys Leu Gly Val Ser
    185                 190                 195

CAG CAA ACT ATC TTT TCT GTT TTT CAT AAT GAT GCT GCT GAG TTG CAT      918
Gln Gln Thr Ile Phe Ser Val Phe His Asn Asp Ala Ala Glu Leu His
200                 205                 210                 215

AAT GTC ACT ACA GAT CTG GAA AAA GTC TGT AGG CAA CTG CAT GAT CCT      966
Asn Val Thr Thr Asp Leu Glu Lys Val Cys Arg Gln Leu His Asp Pro
                220                 225                 230

TCT GTA GGA CTC AGT GAT ATT TCT ATC ACT TTA TTT TCT GCA TCA AAA     1014
Ser Val Gly Leu Ser Asp Ile Ser Ile Thr Leu Phe Ser Ala Ser Lys
            235                 240                 245

CCA ATG CTA GCT GCT ATT GCA GAT ATT GAG CAC ATT GAG AAG GAT ATG     1062
Pro Met Leu Ala Ala Ile Ala Asp Ile Glu His Ile Glu Lys Asp Met
        250                 255                 260

AAA CAT CAG AGT TTC TAC ATA GAA ACC AAG CTA GAT GGT GAA CGT ATG     1110
Lys His Gln Ser Phe Tyr Ile Glu Thr Lys Leu Asp Gly Glu Arg Met
    265                 270                 275

CAA ATG CAC AAA GAT GGA GAT GTA TAT AAA TAC TTC TCT CGA AAT GGA     1158
Gln Met His Lys Asp Gly Asp Val Tyr Lys Tyr Phe Ser Arg Asn Gly
280                 285                 290                 295

TAT AAC TAC ACT GAT CAG TTT GGT GCT TCT CCT ACT GAA GGT TCT CTT     1206
Tyr Asn Tyr Thr Asp Gln Phe Gly Ala Ser Pro Thr Glu Gly Ser Leu
                300                 305                 310

ACC CCA TTC ATT CAT AAT GCA TTC AAA GCA GAT ATA CAA ATC TGT ATT     1254
Thr Pro Phe Ile His Asn Ala Phe Lys Ala Asp Ile Gln Ile Cys Ile
            315                 320                 325

CTT GAT GGT GAG ATG ATG GCC TAT AAT CCT AAT ACA CAA ACT TTC ATG     1302
Leu Asp Gly Glu Met Met Ala Tyr Asn Pro Asn Thr Gln Thr Phe Met
        330                 335                 340

CAA AAG GGA ACT AAG TTT GAT ATT AAA AGA ATG GTA GAG GAT TCT GAT     1350
Gln Lys Gly Thr Lys Phe Asp Ile Lys Arg Met Val Glu Asp Ser Asp
    345                 350                 355

CTG CAA ACT TGT TAT TGT GTT TTT GAT GTA TTG ATG GTT AAT AAT AAA     1398
Leu Gln Thr Cys Tyr Cys Val Phe Asp Val Leu Met Val Asn Asn Lys
360                 365                 370                 375

AAG CTA GGG CAT GAG ACT CTG AGA AAG AGG TAT GAG ATT CTT AGT AGT     1446
Lys Leu Gly His Glu Thr Leu Arg Lys Arg Tyr Glu Ile Leu Ser Ser
                380                 385                 390

ATT TTT ACA CCA ATT CCA GGT AGA ATA GAA ATA GTG CAG AAA ACA CAA     1494
Ile Phe Thr Pro Ile Pro Gly Arg Ile Glu Ile Val Gln Lys Thr Gln
            395                 400                 405

GCT CAT ACT AAG AAT GAA GTA ATT GAT GCA TTG AAT GAA GCA ATA GAT     1542
Ala His Thr Lys Asn Glu Val Ile Asp Ala Leu Asn Glu Ala Ile Asp
        410                 415                 420

AAA AGA GAA GAG GGA ATT ATG GTA AAA CAA CCT CTA TCC ATC TAC AAG     1590
Lys Arg Glu Glu Gly Ile Met Val Lys Gln Pro Leu Ser Ile Tyr Lys
    425                 430                 435

CCA GAC AAA AGA GGT GAA GGG TGG TTA AAA ATT AAA CCA GAG TAT GTC     1638
Pro Asp Lys Arg Gly Glu Gly Trp Leu Lys Ile Lys Pro Glu Tyr Val
440                 445                 450                 455

AGT GGA CTA ATG GAT GAA TTG GAC ATT TTA ATT GTT GGA GGA TAT TGG     1686
Ser Gly Leu Met Asp Glu Leu Asp Ile Leu Ile Val Gly Gly Tyr Trp
```

-continued

```
    Ser Gly Leu Met Asp Glu Leu Asp Ile Leu Ile Val Gly Gly Tyr Trp
                    460                 465                 470

GGT AAA GGA TCA CGG GGT GGA ATG ATG TCT CAT TTT CTG TGT GCA GTA           1734
Gly Lys Gly Ser Arg Gly Gly Met Met Ser His Phe Leu Cys Ala Val
            475                 480                 485

GCA GAG AAG CCC CCT CCT GGT GAG AAG CCA TCT GTG TTT CAT ACT CTC           1782
Ala Glu Lys Pro Pro Pro Gly Glu Lys Pro Ser Val Phe His Thr Leu
        490                 495                 500

TCT CGT GTT GGG TCT GGC TGC ACC ATG AAA GAA CTG TAT GAT CTG GGT           1830
Ser Arg Val Gly Ser Gly Cys Thr Met Lys Glu Leu Tyr Asp Leu Gly
    505                 510                 515

TTG AAA TTG GCC AAG TAT TGG AAG CCT TTT CAT AGA AAA GCT CCA CCA           1878
Leu Lys Leu Ala Lys Tyr Trp Lys Pro Phe His Arg Lys Ala Pro Pro
520                 525                 530                 535

AGC AGC ATT TTA TGT GGA ACA GAG AAG CCA GAA GTA TAC ATT GAA CCT           1926
Ser Ser Ile Leu Cys Gly Thr Glu Lys Pro Glu Val Tyr Ile Glu Pro
                540                 545                 550

TGT AAT TCT GTC ATT GTT CAG ATT AAA GCA GCA GAG ATC GTA CCC AGT           1974
Cys Asn Ser Val Ile Val Gln Ile Lys Ala Ala Glu Ile Val Pro Ser
            555                 560                 565

GAT ATG TAT AAA ACT GGC TGC ACC TTG CGT TTT CCA CGA ATT GAA AAG           2022
Asp Met Tyr Lys Thr Gly Cys Thr Leu Arg Phe Pro Arg Ile Glu Lys
        570                 575                 580

ATA AGA GAT GAC AAG GAG TGG CAT GAG TGC ATG ACC CTG GAC GAC CTA           2070
Ile Arg Asp Asp Lys Glu Trp His Glu Cys Met Thr Leu Asp Asp Leu
    585                 590                 595

GAA CAA CTT AGG GGG AAG GCA TCT GGT AAG CTC GCA TCT AAA CAC CTT           2118
Glu Gln Leu Arg Gly Lys Ala Ser Gly Lys Leu Ala Ser Lys His Leu
600                 605                 610                 615

TAT ATA GGT GGT GAT GAT GAA CCA CAA GAA AAA AAG CGG AAA GCT GCC           2166
Tyr Ile Gly Gly Asp Asp Glu Pro Gln Glu Lys Lys Arg Lys Ala Ala
                620                 625                 630

CCA AAG ATG AAG AAA GTT ATT GGA ATT ATT GAG CAC TTA AAA GCA CCT           2214
Pro Lys Met Lys Lys Val Ile Gly Ile Ile Glu His Leu Lys Ala Pro
            635                 640                 645

AAC CTT ACT AAC GTT AAC AAA ATT TCT AAT ATA TTT GAA GAT GTA GAG           2262
Asn Leu Thr Asn Val Asn Lys Ile Ser Asn Ile Phe Glu Asp Val Glu
        650                 655                 660

TTT TGT GTT ATG AGT GGA ACA GAT AGC CAG CCA AAG CCT GAC CTG GAG           2310
Phe Cys Val Met Ser Gly Thr Asp Ser Gln Pro Lys Pro Asp Leu Glu
    665                 670                 675

AAC AGA ATT GCA GAA TTT GGT GGT TAT ATA GTA CAA AAT CCA GGC CCA           2358
Asn Arg Ile Ala Glu Phe Gly Gly Tyr Ile Val Gln Asn Pro Gly Pro
680                 685                 690                 695

GAC ACG TAC TGT GTA ATT GCA GGG TCT GAG AAC ATC AGA GTG AAA AAC           2406
Asp Thr Tyr Cys Val Ile Ala Gly Ser Glu Asn Ile Arg Val Lys Asn
                700                 705                 710

ATA ATT TTG TCA AAT AAA CAT GAT GTT GTC AAG CCT GCA TGG CTT TTA           2454
Ile Ile Leu Ser Asn Lys His Asp Val Val Lys Pro Ala Trp Leu Leu
            715                 720                 725

GAA TGT TTT AAG ACC AAA AGC TTT GTA CCA TGG CAG CCT CGC TTT ATG           2502
Glu Cys Phe Lys Thr Lys Ser Phe Val Pro Trp Gln Pro Arg Phe Met
        730                 735                 740

ATT CAT ATG TGC CCA TCA ACC AAA GAA CAT TTT GCC CGT GAA TAT GAT           2550
Ile His Met Cys Pro Ser Thr Lys Glu His Phe Ala Arg Glu Tyr Asp
    745                 750                 755

TGC TAT GGT GAT AGT TAT TTC ATT GAT ACA GAC TTG AAC CAA CTG AAG           2598
Cys Tyr Gly Asp Ser Tyr Phe Ile Asp Thr Asp Leu Asn Gln Leu Lys
760                 765                 770                 775
```

```
GAA GTA TTC TCA GGA ATT AAA AAT TCT AAC GAG CAG ACT CCT GAA GAA    2646
Glu Val Phe Ser Gly Ile Lys Asn Ser Asn Glu Gln Thr Pro Glu Glu
            780                 785                 790

ATG GCT TCT CTG ATT GCT GAT TTA GAA TAT CGG TAT TCC TGG GAT TGC    2694
Met Ala Ser Leu Ile Ala Asp Leu Glu Tyr Arg Tyr Ser Trp Asp Cys
        795                 800                 805

TCT CCT CTC AGT ATG TTT CGA CGC CAC ACC GTT TAT TTG GAC TCG TAT    2742
Ser Pro Leu Ser Met Phe Arg Arg His Thr Val Tyr Leu Asp Ser Tyr
    810                 815                 820

GCT GTT ATT AAT GAC CTG AGT ACC AAA AAT GAG GGG ACA AGG TTA GCT    2790
Ala Val Ile Asn Asp Leu Ser Thr Lys Asn Glu Gly Thr Arg Leu Ala
825                 830                 835

ATT AAA GCC TTG GAG CTT CGG TTT CAT GGA GCA AAA GTA GTT TCT TGT    2838
Ile Lys Ala Leu Glu Leu Arg Phe His Gly Ala Lys Val Val Ser Cys
840                 845                 850                 855

TTA GCT GAG GGA GTG TCT CAT GTA ATA ATT GGG GAA GAT CAT AGT CGT    2886
Leu Ala Glu Gly Val Ser His Val Ile Ile Gly Glu Asp His Ser Arg
                860                 865                 870

GTT GCA GAT TTT AAA GCT TTT AGA AGA ACT TTT AAG AGA AAG TTT AAA    2934
Val Ala Asp Phe Lys Ala Phe Arg Arg Thr Phe Lys Arg Lys Phe Lys
            875                 880                 885

ATC CTA AAA GAA AGT TGG GTA ACT GAT TCA ATA GAC AAG TGT GAA TTA    2982
Ile Leu Lys Glu Ser Trp Val Thr Asp Ser Ile Asp Lys Cys Glu Leu
        890                 895                 900

CAA GAA GAA AAC CAG TAT TTG ATT TAAAGCTAGG TTTCCTAGTG AGGAAAGCCT   3036
Gln Glu Glu Asn Gln Tyr Leu Ile
    905                 910

CTGATCTGGC AGACTCATTG CAGCAGGTGG TAATGATAAA ATACTAAACT ACATTTTATT   3096

TTTGTATCTT AAAAATCTAT GCCTAAAAAG TATCATTACA TATAGGAAAA CAATAATTTT   3156

AACTTTTAAG GTTGAAAAGA CAATAGCCCA AGCCAAGAA AGAAAAATTA TCTTGAATGT   3216

AGTATTCAAT GATTTTTTAT GATCAAGGTG AAATAAACAG TCTAAAGAAG AGGTGTTTTT   3276

ATAATATCCA TATAGAAATC TAGAATTTTT ACTTAGATAC TAATAAAAT              3325

(2) INFORMATION FOR SEQ ID NO:2:

(i) SEQUENCE CHARACTERISTICS:
        (A) LENGTH: 911 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ala Ser Gln Thr Ser Gln Thr Val Ala Ser His Val Pro Phe
  1               5                  10                  15

Ala Asp Leu Cys Ser Thr Leu Glu Arg Ile Gln Lys Ser Lys Gly Arg
                 20                  25                  30

Ala Glu Lys Ile Arg His Phe Arg Glu Phe Leu Asp Ser Trp Arg Lys
             35                  40                  45

Phe His Asp Ala Leu His Lys Asn His Lys Asp Val Thr Asp Ser Phe
         50                  55                  60

Tyr Pro Ala Met Arg Leu Ile Leu Pro Gln Leu Glu Arg Glu Arg Met
 65                  70                  75                  80

Ala Tyr Gly Ile Lys Glu Thr Met Leu Ala Lys Leu Tyr Ile Glu Leu
                 85                  90                  95

Leu Asn Leu Pro Arg Asp Gly Lys Asp Ala Leu Lys Leu Leu Asn Tyr
                100                 105                 110
```

```
Arg Thr Pro Thr Gly Thr His Gly Asp Ala Gly Asp Phe Ala Met Ile
        115                 120                 125

Ala Tyr Phe Val Leu Lys Pro Arg Cys Leu Gln Lys Gly Ser Leu Thr
130                 135                 140

Ile Gln Gln Val Asn Asp Leu Leu Asp Ser Ile Ala Ser Asn Asn Ser
145                 150                 155                 160

Ala Lys Arg Lys Asp Leu Ile Lys Lys Ser Leu Leu Gln Leu Ile Thr
                165                 170                 175

Gln Ser Ser Ala Leu Glu Gln Lys Trp Leu Ile Arg Met Ile Ile Lys
            180                 185                 190

Asp Leu Lys Leu Gly Val Ser Gln Gln Thr Ile Phe Ser Val Phe His
        195                 200                 205

Asn Asp Ala Ala Glu Leu His Asn Val Thr Thr Asp Leu Glu Lys Val
    210                 215                 220

Cys Arg Gln Leu His Asp Pro Ser Val Gly Leu Ser Asp Ile Ser Ile
225                 230                 235                 240

Thr Leu Phe Ser Ala Ser Lys Pro Met Leu Ala Ala Ile Ala Asp Ile
                245                 250                 255

Glu His Ile Glu Lys Asp Met Lys His Gln Ser Phe Tyr Ile Glu Thr
            260                 265                 270

Lys Leu Asp Gly Glu Arg Met Gln Met His Lys Asp Gly Asp Val Tyr
        275                 280                 285

Lys Tyr Phe Ser Arg Asn Gly Tyr Asn Tyr Thr Asp Gln Phe Gly Ala
    290                 295                 300

Ser Pro Thr Glu Gly Ser Leu Thr Pro Phe Ile His Asn Ala Phe Lys
305                 310                 315                 320

Ala Asp Ile Gln Ile Cys Ile Leu Asp Gly Glu Met Met Ala Tyr Asn
                325                 330                 335

Pro Asn Thr Gln Thr Phe Met Gln Lys Gly Thr Lys Phe Asp Ile Lys
            340                 345                 350

Arg Met Val Glu Asp Ser Asp Leu Gln Thr Cys Tyr Cys Val Phe Asp
        355                 360                 365

Val Leu Met Val Asn Asn Lys Lys Leu Gly His Glu Thr Leu Arg Lys
    370                 375                 380

Arg Tyr Glu Ile Leu Ser Ser Ile Phe Thr Pro Ile Pro Gly Arg Ile
385                 390                 395                 400

Glu Ile Val Gln Lys Thr Gln Ala His Thr Lys Asn Glu Val Ile Asp
                405                 410                 415

Ala Leu Asn Glu Ala Ile Asp Lys Arg Glu Glu Gly Ile Met Val Lys
            420                 425                 430

Gln Pro Leu Ser Ile Tyr Lys Pro Asp Lys Arg Gly Glu Gly Trp Leu
        435                 440                 445

Lys Ile Lys Pro Glu Tyr Val Ser Gly Leu Met Asp Glu Leu Asp Ile
    450                 455                 460

Leu Ile Val Gly Gly Tyr Trp Gly Lys Gly Ser Arg Gly Gly Met Met
465                 470                 475                 480

Ser His Phe Leu Cys Ala Val Ala Glu Lys Pro Pro Gly Glu Lys
                485                 490                 495

Pro Ser Val Phe His Thr Leu Ser Arg Val Gly Ser Gly Cys Thr Met
            500                 505                 510

Lys Glu Leu Tyr Asp Leu Gly Leu Lys Leu Ala Lys Tyr Trp Lys Pro
        515                 520                 525

Phe His Arg Lys Ala Pro Pro Ser Ser Ile Leu Cys Gly Thr Glu Lys
```

```
                  530                 535                 540
Pro Glu Val Tyr Ile Glu Pro Cys Asn Ser Val Ile Val Gln Ile Lys
545                 550                 555                 560

Ala Ala Glu Ile Val Pro Ser Asp Met Tyr Lys Thr Gly Cys Thr Leu
                565                 570                 575

Arg Phe Pro Arg Ile Glu Lys Ile Arg Asp Asp Lys Glu Trp His Glu
            580                 585                 590

Cys Met Thr Leu Asp Asp Leu Glu Gln Leu Arg Gly Lys Ala Ser Gly
                595                 600                 605

Lys Leu Ala Ser Lys His Leu Tyr Ile Gly Gly Asp Glu Pro Gln
            610                 615                 620

Glu Lys Lys Arg Lys Ala Ala Pro Lys Met Lys Lys Val Ile Gly Ile
625                 630                 635                 640

Ile Glu His Leu Lys Ala Pro Asn Leu Thr Asn Val Asn Lys Ile Ser
                645                 650                 655

Asn Ile Phe Glu Asp Val Glu Phe Cys Val Met Ser Gly Thr Asp Ser
                660                 665                 670

Gln Pro Lys Pro Asp Leu Glu Asn Arg Ile Ala Glu Phe Gly Gly Tyr
            675                 680                 685

Ile Val Gln Asn Pro Gly Pro Asp Thr Tyr Cys Val Ile Ala Gly Ser
690                 695                 700

Glu Asn Ile Arg Val Lys Asn Ile Ile Leu Ser Asn Lys His Asp Val
705                 710                 715                 720

Val Lys Pro Ala Trp Leu Leu Glu Cys Phe Lys Thr Lys Ser Phe Val
                725                 730                 735

Pro Trp Gln Pro Arg Phe Met Ile His Met Cys Pro Ser Thr Lys Glu
            740                 745                 750

His Phe Ala Arg Glu Tyr Asp Cys Tyr Gly Asp Ser Tyr Phe Ile Asp
            755                 760                 765

Thr Asp Leu Asn Gln Leu Lys Glu Val Phe Ser Gly Ile Lys Asn Ser
770                 775                 780

Asn Glu Gln Thr Pro Glu Met Ala Ser Leu Ile Ala Asp Leu Glu
785                 790                 795                 800

Tyr Arg Tyr Ser Trp Asp Cys Ser Pro Leu Ser Met Phe Arg Arg His
                805                 810                 815

Thr Val Tyr Leu Asp Ser Tyr Ala Val Ile Asn Asp Leu Ser Thr Lys
                820                 825                 830

Asn Glu Gly Thr Arg Leu Ala Ile Lys Ala Leu Glu Leu Arg Phe His
            835                 840                 845

Gly Ala Lys Val Val Ser Cys Leu Ala Glu Gly Val Ser His Val Ile
850                 855                 860

Ile Gly Glu Asp His Ser Arg Val Ala Asp Phe Lys Ala Phe Arg Arg
865                 870                 875                 880

Thr Phe Lys Arg Lys Phe Lys Ile Leu Lys Glu Ser Trp Val Thr Asp
                885                 890                 895

Ser Ile Asp Lys Cys Glu Leu Gln Glu Glu Asn Gln Tyr Leu Ile
            900                 905                 910

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:3:

GCGGGATCCA TGAGACTAAT TCTTCCTCAG                                              30

(2) INFORMATION FOR SEQ ID NO:4:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

GCGCTGCAGT TAAATCAAAT ACTGGTTTTG                                              30

(2) INFORMATION FOR SEQ ID NO:5:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

GCGCCCGGGA TGAGACTAAT TCTTCTCCAG                                              30

(2) INFORMATION FOR SEQ ID NO:6:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

GCGGGTACCT TAAATCAAAT ACTGGTTTTC                                              30

(2) INFORMATION FOR SEQ ID NO:7:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

GCGGAATTCA TGAGACTAAT TCTTCCTCAG                                              30

(2) INFORMATION FOR SEQ ID NO:8:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

```
GCGCTCGAGT CAAGCGTAGT CTGGGACGTC GTATGGGTAA ATCAAATACT GGTTTTGTTC        60
```

(2) INFORMATION FOR SEQ ID NO:9:

(i) SEQUENCE CHARACTERISTICS:
        (A) LENGTH: 642 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Pro Val Glu Asp Ala Cys Trp Lys Pro Gly Gln Lys Val Pro Tyr Leu
1               5                   10                  15

Ala Val Ala Arg Thr Phe Glu Lys Ile Glu Glu Val Ser Ala Arg Leu
            20                  25                  30

Arg Met Val Glu Thr Leu Ser Asn Leu Leu Arg Ser Val Ala Leu
        35                  40                  45

Ser Pro Pro Asp Leu Leu Pro Val Leu Tyr Ser Leu Asn His Leu Gly
    50                  55                  60

Pro Pro Gln Gln Gly Leu Glu Leu Gly Val Gly Asp Gly Val Leu Leu
65                  70                  75                  80

Lys Ala Val Ala Gln Ala Thr Gly Arg Gln Leu Glu Ser Val Arg Ala
                85                  90                  95

Glu Ala Ala Glu Lys Gly Asp Val Gly Leu Val Ala Glu Asn Ser Arg
            100                 105                 110

Ser Thr Gln Arg Leu Met Leu Pro Pro Pro Leu Thr Ala Ser Gly
        115                 120                 125

Val Phe Ser Lys Phe Arg Asp Ile Ala Arg Leu Thr Gly Ser Ala Ser
    130                 135                 140

Thr Ala Lys Lys Ile Asp Ile Ile Lys Gly Leu Phe Val Ala Cys Arg
145                 150                 155                 160

His Ser Glu Ala Arg Phe Ile Ala Arg Ser Leu Ser Gly Arg Leu Arg
                165                 170                 175

Leu Gly Leu Ala Glu Gln Ser Val Leu Ala Ala Leu Ser Gln Ala Val
            180                 185                 190

Ser Leu Thr Pro Pro Gly Gln Glu Phe Pro Pro Ala Met Val Asp Ala
        195                 200                 205

Gly Lys Gly Lys Thr Ala Glu Ala Arg Lys Thr Trp Leu Glu Glu Gln
    210                 215                 220

Gly Met Ile Leu Lys Gln Thr Phe Cys Glu Val Pro Asp Leu Asp Arg
225                 230                 235                 240

Ile Ile Pro Val Leu Leu Glu His Gly Leu Glu Arg Leu Pro Glu His
                245                 250                 255

Cys Lys Leu Ser Pro Gly Ile Pro Leu Lys Pro Met Leu Ala His Pro
            260                 265                 270

Thr Arg Gly Ile Ser Glu Val Leu Lys Arg Phe Glu Glu Ala Ala Phe
        275                 280                 285

Thr Cys Glu Tyr Lys Tyr Asp Gly Gln Arg Ala Gln Ile His Ala Leu
    290                 295                 300

Glu Gly Gly Glu Val Lys Ile Phe Ser Arg Asn Gln Glu Asp Asn Thr
305                 310                 315                 320

Gly Lys Tyr Pro Asp Ile Ile Ser Arg Ile Pro Lys Ile Lys Leu Pro
                325                 330                 335
```

```
Ser Val Thr Ser Phe Ile Leu Asp Thr Glu Ala Val Ala Trp Asp Arg
            340                 345                 350

Glu Lys Lys Gln Ile Gln Pro Phe Gln Val Leu Thr Thr Arg Lys Arg
            355                 360                 365

Lys Glu Val Asp Ala Ser Glu Ile Gln Val Gln Val Cys Leu Tyr Ala
            370                 375                 380

Phe Asp Leu Ile Tyr Leu Asn Gly Glu Ser Leu Val Arg Glu Pro Leu
385                 390                 395                 400

Ser Arg Arg Arg Gln Leu Leu Arg Glu Asn Phe Val Glu Thr Glu Gly
            405                 410                 415

Glu Phe Val Phe Ala Thr Ser Leu Asp Thr Lys Asp Ile Glu Gln Ile
            420                 425                 430

Ala Glu Phe Leu Glu Gln Ser Val Lys Asp Ser Cys Glu Gly Leu Met
            435                 440                 445

Val Lys Thr Leu Asp Val Asp Ala Thr Tyr Glu Ile Ala Lys Arg Ser
            450                 455                 460

His Asn Trp Leu Lys Leu Lys Asp Tyr Leu Asp Gly Val Gly Asp
465                 470                 475                 480

Thr Leu Asp Leu Val Val Ile Gly Ala Tyr Leu Gly Arg Gly Lys Arg
            485                 490                 495

Ala Gly Arg Tyr Gly Gly Phe Leu Leu Ala Ser Tyr Asp Glu Asp Ser
            500                 505                 510

Glu Glu Leu Gln Ala Ile Cys Lys Leu Gly Thr Gly Phe Ser Asp Glu
            515                 520                 525

Glu Leu Glu Glu His His Gln Ser Leu Lys Ala Leu Val Leu Pro Ser
            530                 535                 540

Pro Arg Pro Tyr Val Arg Ile Asp Gly Ala Val Ile Pro Asp His Trp
545                 550                 555                 560

Leu Asp Pro Ser Ala Val Trp Glu Val Lys Cys Ala Asp Leu Ser Leu
            565                 570                 575

Ser Pro Ile Tyr Pro Ala Ala Arg Gly Leu Val Asp Ser Asp Lys Gly
            580                 585                 590

Ile Ser Leu Arg Phe Pro Arg Phe Ile Arg Val Arg Glu Asp Lys Gln
            595                 600                 605

Pro Glu Gln Ala Thr Thr Ser Ala Gln Val Ala Cys Leu Tyr Arg Lys
            610                 615                 620

Gln Ser Gln Ile Gln Asn Gln Gln Gly Glu Asp Ser Gly Ser Asp Pro
625                 630                 635                 640

Glu Asp
```